United States Patent [19]
Laufer

[11] Patent Number: 6,071,303
[45] Date of Patent: Jun. 6, 2000

[54] DEVICE FOR THE TREATMENT OF INFARCTED TISSUE AND METHOD OF TREATING INFARCTED TISSUE

[75] Inventor: Michael D. Laufer, Menlo Park, Calif.

[73] Assignee: Hearten Medical, Inc., Tustin, Calif.

[21] Appl. No.: 08/768,607

[22] Filed: Dec. 8, 1996

[51] Int. Cl.$^7$ .................................................. A61B 17/36
[52] U.S. Cl. .............................. 607/96; 607/50; 606/27; 606/41
[58] Field of Search .................... 606/38, 3, 27, 606/28, 32, 34, 41, 52; 607/96, 50; 600/508, 439

[56] References Cited

U.S. PATENT DOCUMENTS

| | | |
|---|---|---|
| 4,140,130 | 2/1979 | Storm, III ............................ 128/404 |
| 4,306,561 | 12/1981 | Medinaceli . |
| 4,620,550 | 11/1986 | Doroshuk . |
| 4,738,250 | 4/1988 | Fulkerson et al. . |
| 4,765,331 | 8/1988 | Petruzzi et al. ................. 128/303.14 |
| 4,807,620 | 2/1989 | Strul et al. ............................ 128/303 |
| 4,854,320 | 8/1989 | Dew et al. ............................ 128/397 |
| 4,989,617 | 2/1991 | Memberg et al. .................... 128/785 |
| 5,114,423 | 5/1992 | Kasprzyk et al. ....................... 606/27 |
| 5,129,895 | 7/1992 | Vassiliadis et al. ...................... 606/6 |
| 5,133,365 | 7/1992 | Heil, Jr. et al. ....................... 128/786 |
| 5,143,063 | 9/1992 | Fellner ................................ 128/399 |
| 5,176,135 | 1/1993 | Fain et al. ............................ 128/419 |
| 5,178,145 | 1/1993 | Rea ..................................... 128/642 |
| 5,190,517 | 3/1993 | Zieve et al. ........................... 604/22 |
| 5,230,349 | 7/1993 | Langberg ............................. 128/786 |
| 5,246,438 | 9/1993 | Langberg ............................... 606/33 |
| 5,259,394 | 11/1993 | Bens ................................... 607/127 |
| 5,261,878 | 11/1993 | Galindo ................................. 604/96 |
| 5,281,218 | 1/1994 | Imran ................................... 606/41 |
| 5,292,332 | 3/1994 | Lee ..................................... 606/213 |
| 5,295,955 | 3/1994 | Rosen et al. ........................... 604/22 |
| 5,304,169 | 4/1994 | Sand .................................... 606/5 |
| 5,311,873 | 5/1994 | Savard et al. ........................ 128/696 |
| 5,314,466 | 5/1994 | Stern et al. ........................... 607/156 |
| 5,323,781 | 6/1994 | Ideker et al. . |
| 5,370,677 | 12/1994 | Rudie et al. ........................... 607/101 |
| 5,370,678 | 12/1994 | Edwards et al. ....................... 607/101 |
| 5,405,346 | 4/1995 | Grundy et al. .......................... 606/41 |
| 5,409,479 | 4/1995 | Dew et al. ............................... 606/9 |
| 5,431,646 | 7/1995 | Vassiliadis et al. ...................... 606/6 |
| 5,431,649 | 7/1995 | Mulier et al. .......................... 606/41 |
| 5,437,664 | 8/1995 | Cohen et al. .......................... 606/42 |
| 5,447,529 | 9/1995 | Marchlinski et al. . |
| 5,454,807 | 10/1995 | Lennox et al. ......................... 606/15 |
| 5,454,809 | 10/1995 | Janssen ................................. 606/41 |
| 5,458,596 | 10/1995 | Lax et al. .............................. 606/31 |
| 5,462,545 | 10/1995 | Wang et al. ........................... 606/41 |
| 5,484,432 | 1/1996 | Sand .................................... 606/5 |
| 5,498,260 | 3/1996 | Rink et al. ............................ 606/16 |
| 5,522,873 | 6/1996 | Jackman et al. ...................... 607/122 |
| 5,529,067 | 6/1996 | Larsen et al. ......................... 128/642 |
| 5,540,679 | 7/1996 | Fram et al. ............................ 606/27 |
| 5,549,640 | 8/1996 | Fontenot . |
| 5,551,427 | 9/1996 | Altman . |
| 5,558,671 | 9/1996 | Yates .................................... 606/38 |
| 5,571,216 | 11/1996 | Anderson .............................. 623/66 |
| 5,591,157 | 1/1997 | Hennings et al. ........................ 606/3 |
| 5,662,643 | 9/1997 | Kung et al. ............................. 606/3 |
| 5,752,518 | 5/1998 | McGee et al. . |

*Primary Examiner*—Marvin M. Lateef
*Assistant Examiner*—Shawna J Shaw
*Attorney, Agent, or Firm*—Burns, Doane, Swecker & Mathis LLP

[57] ABSTRACT

A device and method for treating myocardial infarction by selectively heating the infarct scar to reduce the size of the scar tissue area by shrinking the tissue in the heart, stiffen the floppy portion of the scar tissue, reduce the ventricular systolic wall tension, and increase the overall pumping efficiency of the infarcted heart by eliminating a ventricular aneurism, if present. The heat can be applied to or induced in the infarct scar. Force can also be applied to assist the reduction of the size of the scar area using the device of the present invention which has a heating element and a scissor-like clamp for squeezing two portions of the infarct scar together.

15 Claims, 4 Drawing Sheets

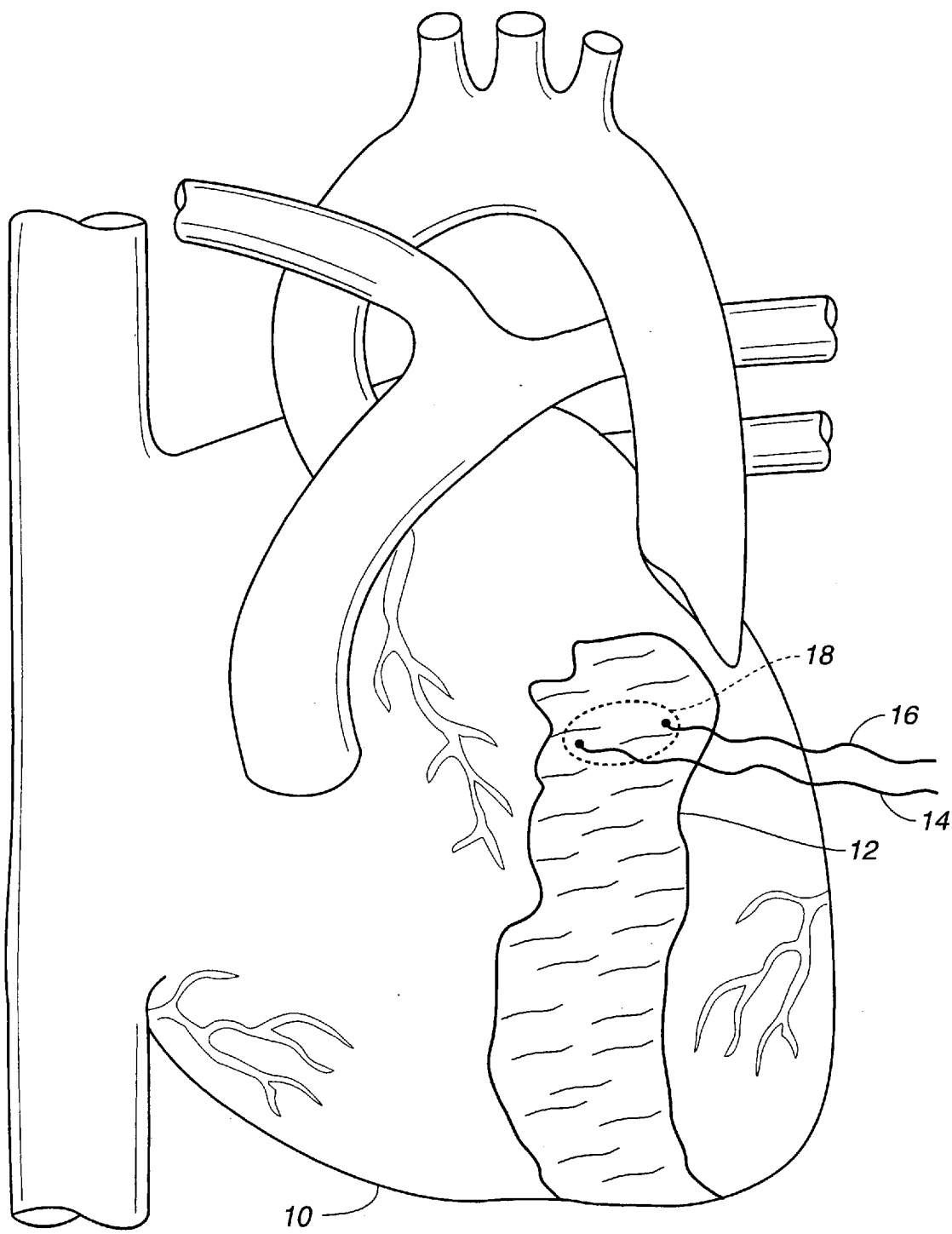
FIG._1

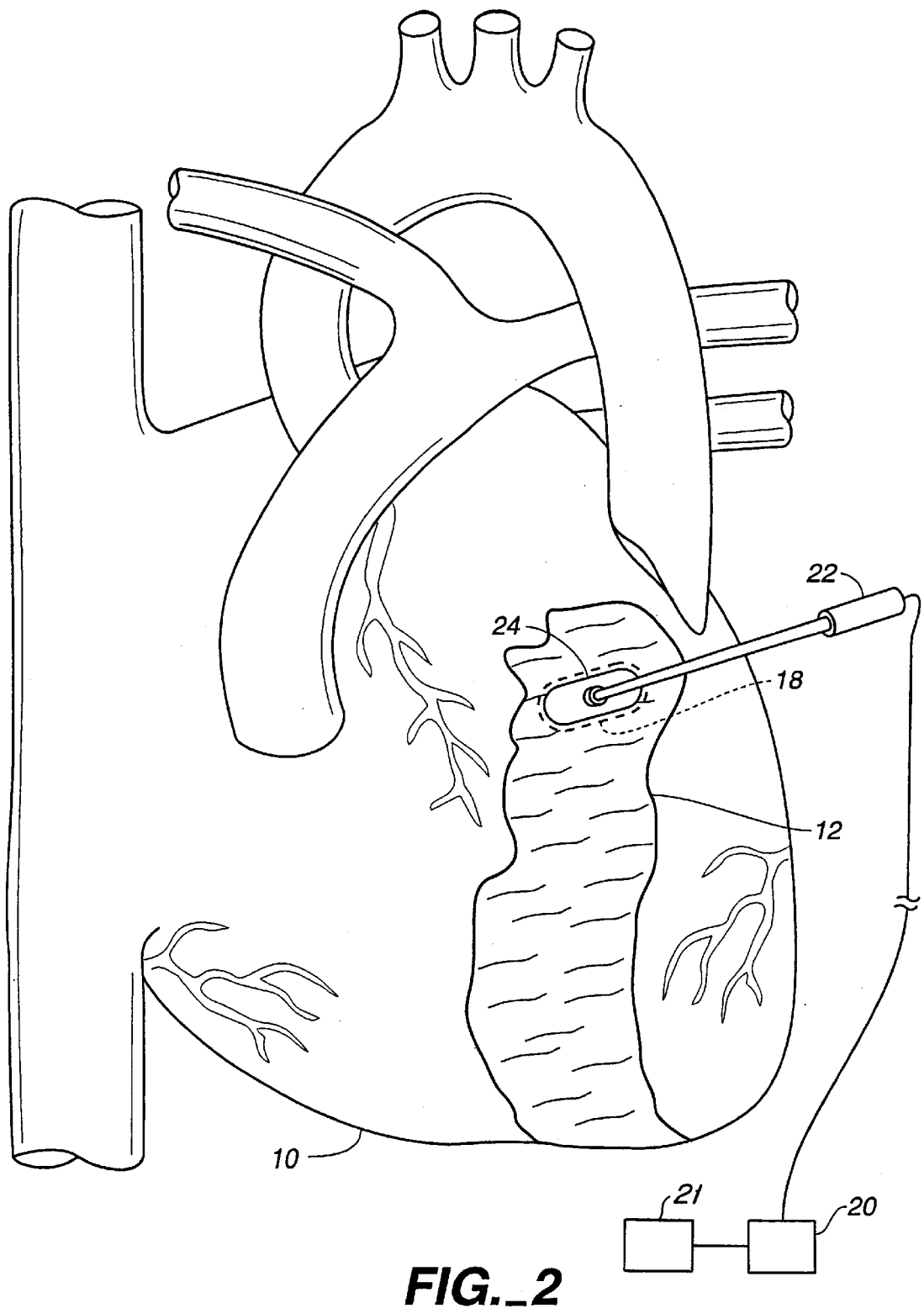
FIG._2

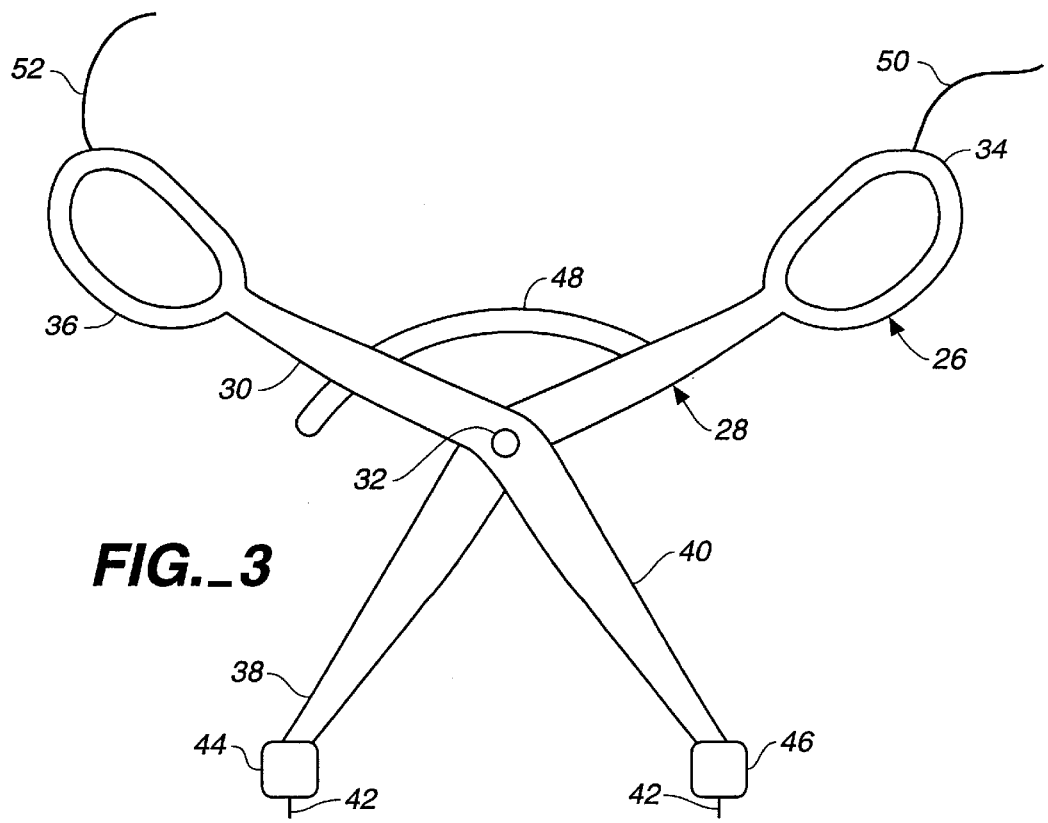
FIG._3
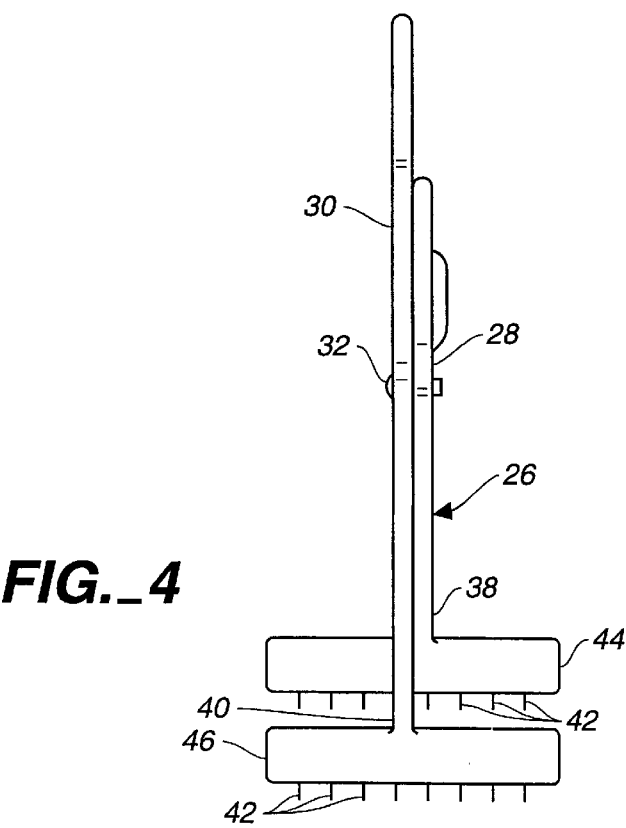
FIG._4

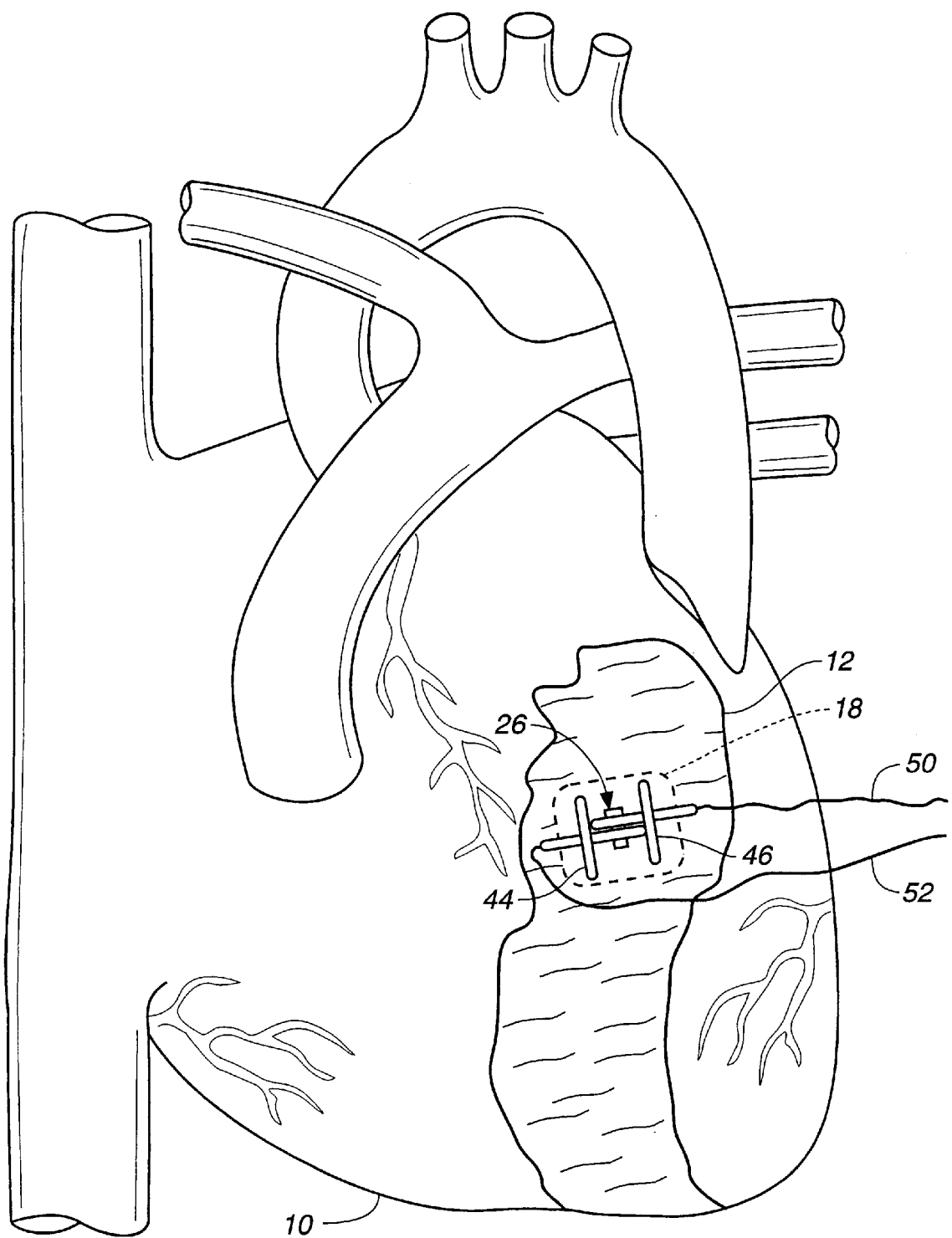
FIG._5

DEVICE FOR THE TREATMENT OF INFARCTED TISSUE AND METHOD OF TREATING INFARCTED TISSUE

FIELD OF THE INVENTION

The present invention is related generally to the modification of heart tissue for the treatment of myocardial infarction.

BACKGROUND OF THE INVENTION

As is well known, the heart has four chambers for receiving and pumping blood to various parts of the body. During normal operation of the heart, oxygen-poor blood returning from the body enters the right atrium. The right atrium fills with blood and eventually contracts to expel the blood through the tricuspid valve to the right ventricle. Contraction of the right ventricle ejects the blood in a pulse-like manner into the pulmonary artery and each lung. The oxygenated blood leaves the lungs through the pulmonary veins and fills the left atrium. The left atrium fills with blood and eventually contracts to expel the blood through the mitral valve to the left ventricle. Contraction of the left ventricle forces blood through the aorta to eventually deliver the oxygenated blood to the rest of the body.

Myocardial infarction (i.e., heart attack) can result in congestive heart failure. Congestive heart failure is a condition wherein the heart can not pump enough blood. When patients have a heart attack, part of the circulation to the heart wall muscle is lost usually do to a blood clot which dislodges from a larger artery and obstructs a coronary artery. If the clot is not dissolved within about 3 to 4 hours, the muscle which lost its blood supply necroses and subsequently becomes a scar. The scarred muscle is not contractile, therefore it does not contribute, to the pumping ability of the heart. In addition, the scarred muscle is elastic (i.e., floppy) which further reduces the efficiency of the heart because a portion of the force created by the remaining healthy muscle bulges out the scarred tissue (i.e., ventricular aneurism) instead of pumping the blood out of the heart.

Congestive heart failure is generally treated with lots of rest, a low-salt diet, and medications such as A.C.E. inhibitors, digitalis, vasodilators and diuretics. In some myocardial infarction instances, the scarred muscle is cut out of the heart and the remaining portions of the heart are sutured (i.e., aneurismechtomy). In limited circumstances a heart transplant may be performed.

Collagen-containing tissue is ubiquitous in the human body and makes up a substantial portion of the scar. Collagen demonstrates several unique characteristics not found in other tissues. Intermolecular cross links provide collagen-containing tissue with unique physical properties of high tensile strength and substantial elasticity. A property of collagen is shrinkage of collagen fibers when elevated in temperature. This molecular response to temperature elevation is believed to be the result of rupture of the collagen stabilizing cross links and immediate contraction of the collagen fibers to about one-third of their original linear dimension or the result of a change in the hydration of the tissue. Another property of collagen is that the caliber of the individual fibers increases greatly, over four fold, without changing the structural integrity of the connective tissue.

There has been discussion in the existing literature regarding alteration of collagen-containing tissue in different parts of the body. One known technique for effective use of this knowledge of the properties of collagen is through the use of infrared laser energy to effect tissue heating. The use of infrared laser energy as a corneal collagen shrinking tool of the eye has been described and relates to laser keratoplasty, as set forth in U.S. Pat. No. 4,976,709. The importance of controlling the localization, timing of laser energy delivery is recognized as paramount in providing the desired soft tissue shrinkage effects without creating excessive damage to the surrounding non-target tissues. Another known technique of altering collagen is described in U.S. Pat. No. 5,458,596 to treat joints. U.S. Pat. No. 5,437,664 describes using a catheter for venous occlusion and coagulation of blood.

Thermal destruction (i.e., ablation) of problematic myocardial tissue (i.e., arrhythmogenic focus) is a therapeutic procedure used with increasing frequency for the treatment of cardiac arrhythmias (e.g., ventricular tachycardia) as described in U.S. Pat. No. 5,246,438. The treatment of cardiac arrhythmias involves treating electrically problematic but otherwise healthy tissue. As a result one goal of ablation is to localize the heat as much as possible so as to restrict the ablation to only the problematic healthy tissue.

SUMMARY OF THE INVENTION

The present invention provides a device and method for treating infarct scar tissue of a mammalian heart by selectively heating the infarct scar to reduce the size of the scar tissue surface area, increase the cross-section of the scar tissue, stiffen the floppy portion of the scar tissue, reduce the ventricular systolic wall tension, and increase the overall pumping efficiency of the infarcted heart by eliminating the ventricular aneurism, if present. It is an objective of the present invention to not affect the healthy heart tissue or ablate the infarcted tissue. Furthermore, it is an objective of the present invention to diffuse the heat over the infarcted area.

The method is similar to an annealing process wherein the scar tissue undergoes heating and then is allowed to cool slowly. The heat can be applied to or induced in the infarct scar. Force can also be applied in accordance with the present invention to assist the reduction of the size of the scar. Generally speaking, besides reducing the surface area of the scarred tissue, the present invention alters the material properties of the infarct scar such as making it stiffer and less elastic.

In one aspect of the invention, there is provided an apparatus for heating an infarct scar in a heart having a heating element having a projection for piercing the scar and a mechanism for squeezing at least two portions of the scar toward each other.

In another aspect of the invention, there is provided a method for treating an infarct scar in a heart including the step of energizing a heating element to raise the temperature of the infarct scar to a temperature sufficient to reduce the surface area of the infarct scar.

In yet another aspect of the invention, there is provided a method for training a person to perform a method for treating an infarct scar in a heart including the steps of demonstrating or instructing how to do the following step of energizing a heating element to raise the temperature of the infarct scar to a temperature sufficient to reduce the surface area of the infarct scar.

In still another aspect of the invention, there is provided a modified mammalian heart having a contracted infarct scar tissue portion diminished in its surface area and stiffened.

In yet another aspect of the invention, there is provided a method for treating an infarct scar in a heart including the step of energizing a heating element to raise the temperature of the infarct scar to a temperature sufficient to reduce the ventricular systolic wall tension.

BRIEF DESCRIPTION OF THE DRAWINGS

As used herein, like reference numerals will designate similar elements in the various embodiments of the present invention wherein:

FIG. 1 is a mammalian heart with electrodes inserted in an infarcted area;

FIG. 2 is a mammalian heart with a radio-frequency heating element in contact with the infarcted area;

FIG. 3 is a front view of a device for heating and squeezing portions of the infarcted area together;

FIG. 4 is a side view of the device of FIG. 3; and

FIG. 5 is a top view of the device of FIG. 2 during treatment of the infarcted area.

DETAILED DESCRIPTION OF THE PREFERRED EMBODIMENTS

The present invention provides a device and method for altering the material properties of collagen-containing infarcted tissue in a patient's heart. There also is provided a method of training a person to perform a method for treating an infarct scar in a mammalian heart. The invention is used to accurately control the inducement of heat or application of heat within a specific thermal range, and deliver thermal energy to the collagen-containing infarcted tissue to reduce the size of the scar tissue area by shrinking the infarcted tissue in the heart and stiffening the floppy portion of the scar tissue without ablating the tissue. As a result, the overall pumping efficiency of the infarcted heart is increased. Likewise, a modified mammalian heart having a contracted infarct scar tissue portion diminished in its surface area and reduced ventricular systolic wall tension results.

Referring initially to FIG. 1, there is illustrated a heart 10 having an infarcted region or portion 12. The infarcted portion 12 of the heart can be accessed with conventional open chest surgery or with arthroscopic techniques. A positive electrode 14 and negative electrode 16 are inserted in a portion of the infarcted portion 12 to induce resistive heating in the infarct scar in the desired treatment area 18 when energy is applied across the electrodes. Alternatively, the positive and negative electrodes can be placed in contact with the infarcted scar. The positive and negative electrodes function as a heating element as they are energized to raise the temperature of the scar in the desired treatment area 18 to a temperature sufficient to reduce the surface area of the scar without ablating the scar tissue or damaging the healthy tissue surrounding the infarcted portion 12. The term "heating element" as used herein encompasses elements that apply energy thereby inducing heat in the tissue as well as to elements that apply heat to the tissue. In a preferred embodiment, the scar is heated to a temperature in the range of about 40 degrees Celsius to about 75 degrees Celsius, more preferably about 60 degrees Celsius to about 65 degrees Celsius. After the desired treatment area 18 has been heated, it is allowed to cool. Energy is no longer applied after there has been sufficient shrinkage of the scar tissue. Sufficient shrinkage may be detected visually, mechanically, echocardiograhically, ventriculographically with x-ray, fluoroscopically or with appropriate feed back variables, such as impedance monitoring, temperature monitoring, or any other suitable method. The electrodes or heating element can then be moved to another portion of the infarcted portion 12 for treatment. It is believed, without being limited to a particular theory, that as the infarct scar is heated the collagen fibers straighten then as the collagen fibers cool they re-entwine or refold around each other becoming shorter, tighter, thicker, stronger, stiffer, or some combination of these qualities.

The method is contemplated to be used with any suitable appliance for applying radiant energy, thermal energy, or to otherwise heat the infarcted tissue and reduce the area of the infarcted tissue. For example, a radio-frequency generator 20 and heating element applicator 22 can be used (FIG. 2). When the heating element 24 of the applicator 22 is positioned at the desired treatment site, the radio-frequency generator 20 is activated to provide suitable energy, preferably at a selected frequency in the range of 10 megahertz to 1000 megahertz, to heat the scar tissue to a temperature sufficient to reduce the surface area of the scar without ablating the scar tissue or damaging the healthy tissue surrounding the infarcted area 12. A feedback indicator 21 can be connected to the heating element applicator for detecting appropriate feedback variables. Preferably, the emitted energy is converted within the scar tissue into heat in the range of about 40 degrees Celsius to about 75 degrees Celsius, more preferably in the range of about 60 degrees Celsius to about 65 degrees Celsius. The radio-frequency energy is preferably applied at low power levels (e.g., 1 to 20 watts). Suitable radio-frequency power sources are readily commercially available. In one embodiment, the radio-frequency generator 20 has a single channel, delivering approximately 1 to 20 watts of energy and possessing continuous delivery capability.

The heating element 24 of the applicator 22, as shown in FIG. 2, operates as a unipolar electrode. An outer electrode (not shown) having a much larger surface area than the heating element 24 is placed on the outer surface of the patient's body. For example, an external metal mesh or solid plate is placed on the skin. Both electrodes are connected to radio-frequency generator 20 which produces an electric field at a high frequency within the patient's body. Because the surface area of the heating element 24 is much smaller than that of the outer electrode, the density of the high frequency electric field is much higher around the heating element. The electric field reaches its highest density between the two electrodes in the region near the heating element 24. The increased density of the field around the heating element 24 produces localized heating of the scar tissue in the treatment area 18. Alternatively, two electrodes can be placed on the scar and energized in a bipolar fashion.

Referring to FIGS. 3–5, another embodiment for a heating device is shown. The heating device of FIGS. 3–5 is comprised of a scissor-like clamp 26 having crossing arms 28 and 30 which are connected by pin 32 near the mid-point of the arms. At the proximal end of arms 28 and 30 are handles 34 and 36, respectively, and at their distal ends 38 and 40, respectively, a plurality of protrusions 42 spaced along elongated members 44 and 46, respectively. An optional releasable lock 48 is located between arms 28 and 30. Likewise, an optional fixed force spring can be located between the arms. Attached to arm 28 is a positive electrode 50 and attached to arm 30 is negative electrode 52. Each of the arms 28 and 30 are free to rotate about pin 32 and are electrically isolated from each other such that when a potential is applied between the electrodes 50 and 52 there is no short between the arms.

The clamp 26 is used by a surgeon (or an individual demonstrating) to squeeze and shrink a portion of the area of the infarct scar tissue 12. (Likewise, an individual can instruct a surgeon on how to accomplish the method of the present invention with the clamp 26 or other embodiments disclosed herein.) The surgeon grabs (or pierces the scar tissue with the protrusions 42, if present) and squeezes the two portions of the scar tissue toward each other by actuating the clamp with the handles 34 and 36 (FIG. 5). The protrusions 42 when present are conductive elements. The positive and negative electrodes are then energized by the surgeon to function as a heating element to raise the temperature of the scar in the desired treatment area 18 to a temperature sufficient to reduce the surface area of the scar without ablating the scar tissue or damaging the healthy tissue surrounding the infarcted portion 12. The protrusions can be used to treat endocardial, sub-endocardial and transmural infarcted areas. The protrusions can have insulated proximal portions such that the distal portions are used to treat endocardial infarcted areas. Alternatively, the protrusions can have insulated distal portions such that the proximal portions are used to treat sub-endocardial infarcted areas. The protrusions can be uninsulated to treat transmural infarcted areas. Likewise, only a portion of a side of a protrusion may be insulated.

The clamp 26 is beneficial in applying force to the infarcted tissue to assist in the shrinking process. The releasable lock 48 or fixed force spring can be used to preset the distance which the two portions of the scar are going to be moved toward each other. Alternatively, the releasable lock can be used to hold the two portions steady at a given distance during the heating process. The elongated members 44 and 46 are generally not brought close together so that a larger area of the scar can be treated. Generally, the elongated members 44 and 46 are actuated toward each other so as to apply a relatively small amount of force to assist the shrinking process. The clamp 26 illustrated in FIGS. 3–5 utilizes resistive heating of the scar tissue, but it is also within the scope of the invention that a radio-frequency generator and electrodes, as well as other means to be described below, can be utilized.

The heating element of any of the embodiments can be made to provide protection against overheating of the scar tissue. Techniques, for example temperature monitoring or electrical characteristic monitoring (e.g., impedance), can be utilized in a system which shuts down the application of energy to the heating element to avoid ablating the tissue or damaging healthy tissue. The surgeon can, if desired, override the feedback control system. A microprocessor can be included and incorporated into the feedback control system to switch the power on and off, as well as modulate the power. The microprocessor can serve as a controller to watch the temperature and modulate the power in order to avoid over-heating of the tissue. The heating element can be synchronized with the ECG so that the heart wall is in diastole. Furthermore, the system can include auditory or visual feedback indicators for signalling when shrinkage, temperature, or other variables are occurring and also when any have reached or exceeded desired conditions.

It is to be understood that other forms of energy, in addition to those discussed above, such as microwaves, ultrasound, and light (either coherent or incoherent sources) can be used, and that the thermal energy generated from a hot fluid element (e.g., liquids, gases, combinations of liquids and gases, etc.), a curie point element, or similar elements can be used as well. Heating element 42 in accordance with any of the embodiments can be a number of different materials including but not limited to conductive polymer, stainless steel, platinum, or other noble metals.

While several particular embodiments of the invention have been illustrated and described, it will be apparent that various modifications can be made without departing from the spirit and scope of the invention. Accordingly, it is not intended that the invention be limited, except as by the appended claims.

What is claimed is:

1. A method for treating an infarct scar in a heart, comprising the steps of:
    locating and isolating an infarct scar on a mammalian heart;
    placing a heating element on a floppy tissue surface of the infarct scar;
    energizing the heating element to raise the temperature of the infarct scar to a temperature sufficient to reduce the surface area of the infarct scar; and
    repeating the placing and energizing steps to treat the entire infarct scar surface.

2. The method of claim 1 further comprising the step of:
    squeezing at least two portions of the infarct scar toward each other.

3. The method of claim 1 further comprising the steps of:
    piercing the scar; and
    squeezing at least two portions of the scar toward each other.

4. The method of claim 1 further comprising the steps of:
    providing an apparatus having a heating element having a projection for piercing the scar and means for squeezing at least two portions of the scar toward each other;
    piercing the scar; and
    squeezing at least two portions of the scar toward each other.

5. The method of claim 1 wherein the heating element is energized by applying radio frequency energy.

6. The method of claim 1 wherein the heating element is energized by resistive heating.

7. The method of claim 1 wherein the scar is energized to a temperature in the range of about 40 degrees Celsius to about 75 degrees Celsius.

8. A method for training a person to perform a method for treating an infarct scar in a heart, comprising the step of:
    demonstrating or instructing the performance of the following steps of:
    locating and isolating an infarct scar on a mammalian heart;
    placing a heating element on a floppy tissue surface of the infarct scar;
    energizing the heating element to raise the temperature of the infarct scar to a temperature sufficient to reduce the surface area of the infarct scar; and
    repeating the placing and energizing steps to treat the entire infarct scar surface.

9. The method of claim 8 further comprising the step of:
    squeezing at least two portions of the infarct scar toward each other.

10. The method of claim 8 further comprising demonstrating or instructing the performance of the following steps of:
    piercing the scar; and
    squeezing at least two portions of the scar toward each other.

11. The method of claim 8 further comprising the steps of:
    providing an apparatus having a heating element having a projection for piercing the scar and means for squeezing at least two portions of the scar toward each other; and demonstrating or instructing the performance of the following steps of:

piercing the scar; and squeezing at least two portions of the scar toward each other.

12. The method of claim 8 Wherein the heating element is energized by applying radio frequency energy.

13. The method of claim 8 wherein the heating element is energized by resistive heating.

14. The method of claim 8 wherein the scar is energized to a temperature in the range of about 40 degrees Celsius to about 75 degrees Celsius.

15. A method for treating an infarct scar in a heart, comprising the steps of:

locating and isolating an infarct scar on a mammalian heart;

placing a heating element on a floppy tissue surface of the infarct scar;

energizing the heating element to raise the temperature of the infarct scar to a temperature sufficient to reduce the ventricular systolic wall tension; and repeating the placing and energizing steps to treat the entire infarct scar surface.

* * * * *